(12) United States Patent
Keller

(10) Patent No.: US 9,989,517 B2
(45) Date of Patent: Jun. 5, 2018

(54) METHODS AND COMPOSITIONS FOR MARKING URINE SAMPLES TO IDENTIFY SOURCE

(71) Applicant: Ruprecht Keller, Schleiden (DE)

(72) Inventor: Ruprecht Keller, Schleiden (DE)

( * ) Notice: Subject to any disclaimer, the term of this patent is extended or adjusted under 35 U.S.C. 154(b) by 200 days.

(21) Appl. No.: 14/392,346

(22) PCT Filed: Jun. 27, 2014

(86) PCT No.: PCT/US2014/044533
§ 371 (c)(1),
(2) Date: Dec. 23, 2015

(87) PCT Pub. No.: WO2014/210434
PCT Pub. Date: Dec. 31, 2014

(65) Prior Publication Data
US 2016/0178609 A1    Jun. 23, 2016

Related U.S. Application Data

(60) Provisional application No. 61/840,227, filed on Jun. 27, 2013.

(51) Int. Cl.
*G01N 33/493* (2006.01)
*G01N 33/50* (2006.01)
*G01N 30/00* (2006.01)

(52) U.S. Cl.
CPC .......... *G01N 33/493* (2013.01); *G01N 33/50* (2013.01); *G01N 2560/00* (2013.01)

(58) Field of Classification Search
CPC ... G01N 33/493; G01N 33/50; G01N 2560/00
See application file for complete search history.

(56) References Cited

U.S. PATENT DOCUMENTS

| | | | |
|---|---|---|---|
| 4,953,562 A | 9/1990 | Rosen et al. | |
| 5,179,027 A | 1/1993 | Fisher | |
| 2004/0037869 A1* | 2/2004 | Cleverly | A61K 9/0056 424/442 |
| 2004/0166532 A1 | 8/2004 | Keller | |
| 2006/0154297 A1 | 7/2006 | Gauchel | |
| 2015/0369794 A1 | 6/2015 | Keller | |

FOREIGN PATENT DOCUMENTS

| | | |
|---|---|---|
| EP | 2502621 | 9/2012 |
| WO | 2011032584 | 3/2011 |
| WO | WO 2013/078403 | 5/2013 |
| WO | WO 2014/058582 | 4/2014 |

OTHER PUBLICATIONS

Wilson, et al., 1999, "Urinary monitoring of saccharin and acesulfame-K as biomarkers of exposure to these additives". Food Additives & Contaminants, 16(6): 227-238.
"Knauer Application Note: Determination of preservatives in foodstuffs and cosmetics." HPLC SMB Osmometry, updated Aug. 2010.
Zoulias et al., 2000, "Effect of sugar replacement by polyols and acesulfame-K on properties of low-fat cookies". J. Sci. Food Agri. 80:2049-2056.

* cited by examiner

*Primary Examiner* — Jeremy C Flinders
(74) *Attorney, Agent, or Firm* — K&L Gates LLP

(57) ABSTRACT

The present invention is generally related to methods and compositions for uniquely marking individual urine samples to be identifiable to a particular subject either individually or from among a group of subjects.

14 Claims, No Drawings

METHODS AND COMPOSITIONS FOR MARKING URINE SAMPLES TO IDENTIFY SOURCE

This application claims priority to and benefit of International Patent Application No. PCT/US2014/044533, filed Jun. 27, 2014 which in turn claims priority to and benefit U.S. Provisional Application No. 61/840,227, filed Jun. 27, 2013, both of which are herein incorporated by reference in their entireties and for all purposes.

TECHNICAL FIELD

The present invention is generally related to methods and compositions for uniquely marking individual urine samples to be identifiable to a particular subject either individually or from among a group of subjects.

SUMMARY OF THE INVENTION

In one aspect, the present invention provides a method for marking a group of urine samples to identify for each sample the individual who provided that sample by:

(a) orally administering a marker to each individual in a group of individuals, wherein each individual in the group is administered a unique marker, wherein at least one marker (e.g., 2, 3, 4, 5, 6, 7, 8, 9, 10, 15, 25, 50, 100, 250, 500, or more markers) has one or more marker substances that differ in chemical nature, molecular weight, relative amount, or a combination thereof; and wherein at least one of the markers comprises a marker substance selected from the group consisting of acesulfame, an acetylated monoglyceride, butylparaben, povidone, copovidone, crospovidone, gelucire, hypromelloses, polycarbophil, polydextrose, tartaric acid or a salt thereof, and derivatives thereof;

(b) waiting for a length of time sufficient for the marker substances to be present in the urine of the individuals;

(c) collecting a urine sample from each individual;

(d) detecting the presence or amount of the marker substances in the urine samples; and (e) using the presence or amount of the marker substances identified in each sample to identify the individual who provided the sample.

In another aspect, the invention provides a method for marking a urine sample to identify the individual who provided that sample by:

(a) orally administering a marker to an individual, wherein the marker comprises one or more marker substances selected from the group consisting of acesulfame, an acetylated monoglyceride, butylparaben, povidone, copovidone, crospovidone, gelucire, hypromelloses, polycarbophil, polydextrose, tartaric acid or a salt thereof, and derivatives thereof;

(b) waiting for a length of time sufficient for the one or more marker substances to be present in the urine of the individual;

(c) collecting a urine sample from each individual;

(d) detecting the presence or amount of the one or more marker substances in the urine samples; and (e) using the presence or amount of the marker substances identified that the urine sample was obtained from the individual to whom the marker was administered.

In one embodiment of either of the foregoing aspects, the method further comprises detecting the presence or amount of an analyte in the urine sample from the individual or at least one individual within the group of individuals. Although any urinary analyte may be detected and/or measured, particularly useful analytes include, for example, a pharmaceutical, a drug of abuse, nicotine, a performance enhancing drug, and/or metabolites thereof. Drugs of abuse may include, for example, cocaine and heroin. Pharmaceuticals may include, for example, narcotics, pain-killers, sedatives, and stimulants. Performance enhancing drugs may include, for example, erythropoietin, hormones (e.g., steroid hormones and growth hormones), stimulants, and sedatives or tranquilizers.

In some embodiments, the subjects or individuals to whom the a marker is administered is a mammal (e.g., human, horse, dog, etc.).

In another aspect, the present invention provides a set of markers which optionally may be used in any of the foregoing methods. The set of markers has two or more markers suitable for oral administration to a subject, wherein at least one marker of the set (e.g., 2, 3, 4, 5, 6, 7, 8, 9, 10, 15, 25, 50, 100, 250, 500, or more markers) contains one or more marker substances and at least one of the marker substances is acesulfame, an acetylated monoglyceride, butylparaben, povidone, copovidone, crospovidone, gelucire, hypromelloses, polycarbophil, polydextrose, or tartaric acid or a salt thereof, and wherein each marker comprises marker substances that differ in chemical nature, molecular weight, relative amount, or a combination thereof, from other markers in the set such that each marker is unique relative to the other markers in the set.

In some embodiments, the set of markers has at least 2, 3, 4, 5, 6, 7, 8, 9, 10, 15, 25, 50, 100, 250, 500, 750, 1000, or more markers.

In some embodiments, the individual markers of the set may have the same or a different number of marker substances and/or the same or different marker substances. For example, any individual marker independently may have one, two, three, four, five, six, seven, eight, nine, ten, or more different marker substances. When using a marker substance that is normally present in the diet of the subject or is otherwise endogenous (e.g., asulfame and tartaric acid), it may be useful to either administer supraphysiological doses or provide the marker substance with a unique label such as a derivative or containing a stable isotope such that the administered marker substance may be distinguished from naturally-occurring compound.

In some embodiments, the marker substances are substances identifiable and/or quantifiable by enzymatic, immunological, spectrometric, or electrophoretic methods. In one embodiment, the marker substances are detectable by a mass spectrometric method such as LC-MS/MS or GC-MS/MS.

In some embodiments, at least one of the markers further contains at least one polyethylene glycol (PEG) (e.g., a monodispersed or polydispersed PEG). Optionally, at least one of the markers further contains two, three, four, five, six, seven, eight, nine, ten, or more different PEGs of different molecular weight (or average molecular weight).

In some embodiments, the markers are formulated as a capsule, tablet, gelatin capsule ("gel cap"), or other solid form or as a liquid (e.g., a syrup, solution, and suspension) for oral administration to the subject.

By "set" or "set of markers" is meant a plurality of individual markers designed for use together, wherein each marker within the set is administered only to a single individual in a group such that no individual within the group receives the same marker. Typically, each marker within the set will be contained in separate packaging as a unitary dosage form. It is contemplated, however, that one or more markers in the set consist of a plurality of unitary dosages of different marker substances. In some embodiments, each marker of the set is labeled with a unique identifier (e.g., serial number, bar code, RFID tag, etc.), but without an identification of the specific marker or marker contents, such that the unique identifier may be used to correlate the identity of the individual with the specific marker administered.

By "marker" is meant a formulation suitable for oral administration to a subject which contains one or more marker substances, wherein each marker substance is uniquely identifiable from each other marker substance within the marker and within the marker set. In one embodiment, all marker substances that make up the marker are present in a single unitary dosage formulations (i.e., multiple marker substances in a single liquid or solid formulation). It is contemplated, however, that a marker may consist of a plurality of unitary dosage formulations which, when administered substantially simultaneously, function as a marker. For example, a marker that is composed of three marker substances may be presented as a tablet containing two of the marker substances and a second tablet containing the third marker substance.

By "marker substance" is meant a chemical entity which may be orally administered to a subject, absorbed, and excreted in the urine either as the parent compound (i.e., unmetabolized) or as a uniquely identifiable metabolite. In preferred embodiments, the marker substance is not an endogenous molecule or one routinely found in the diet of the subjects and therefore normally would not be found in the urine of the subjects.

By "unitary dosage form" is meant a formulation which is designed to be completely delivered in a single oral administration. For example, liquid formulations may be prepared in a volume of about 5-300 ml, and solid formulations may be prepared as single tablets or capsules.

By "analyte" is meant a urinary compound of interest that is under investigation, other than the marker substances. For example, an analyte may be the parent compound or unique metabolite of an illicit drug, pharmaceutical, or performance enhancing drug.

By "derivative" and/or "derivative thereof," in reference to marker substances, is meant an chemical change to a marker substance identified herein that does not cause an impairment or difference in the functioning of that marker substance in its use in a marker. Marker substance derivatives include, for example, chemical substitutions, additions, or deletions to a marker substance that do not substantially alter the absorption and/or urinary excretion of that marker substance. For example, a derivative of a marker substance may include the addition of a polysaccharide that is cleaved by the gut flora, resulting in the release, absorption, and excretion of the marker substance.

DETAILED DESCRIPTION

Urine analysis is used for a variety of purposes beyond traditional medical diagnostics. In many instances, large numbers of people are screened simultaneously, often outside of a clinical or controlled environment, and/or tested individuals are adversarial to the testing process. For example, workplace testing for illicit drug and other substances has become widespread and a positive result for a banned substance results in a negative consequence (e.g., termination of employment) for the tested subject. Additionally, the governing bodies of competitive sports have become ever more vigilant against the use of performance-enhancing drugs (PEDs), wherein disciplinary action will be taken against an athlete providing a positive sample. Because of the serious negative social and economic implications of this type of testing, there is a need to correctly identify each urine sample with the correct donor subject and to ensure that the urine sample actually contains urine from that subject and actually collected at the time of testing (i.e., an authentic urine sample).

It has been reported that subjects, who knowingly will test positive for a banned substance, attempt to provide an inauthentic urine sample for testing. Subjects providing inauthentic samples often engage in sample substitution for "clean" urine wherein the urine provided for testing is, in fact, urine that the subject collected previously, prior to administration of the banned substance, or even urine collected from another "clean" individual. One method that testing bodies have employed to combat urine substitution is the provision of a supervisor who observes the urine collection process and immediately establishes a chain of custody of the sample. However, the use of an observer is an imperfect solution. A variety of prosthetic devices for surreptitiously holding and dispensing "clean" urine have been developed and this system does not guard against a conspiracy between the observer and the tested subject. There are several secondary problems with the use of a direct observer for urine collection. First, this system is very labor-intensive and time-consuming when a large number of subjects require testing because of the large number of observers required. Second, many people find it objectionable to be observed when providing a urine sample.

Sample Authenticity and Detecting Sample Substitution

The present invention provides methods and compositions to improve or eliminate the problem of urine sample substitution. Specifically, urine substitution may be detected and/or deterred by administering to the test subject, shortly before collecting a urine sample, a formulation (i.e., a marker) which contains one or more marker substances which are rapidly and stoichiometrically excreted in the urine either as the parent marker substance (i.e., unmetabolized) or as a uniquely-identifiable metabolite. The subject must wait a sufficient duration of time for the marker substances to be excreted in the urine before collecting the urine sample and, preferably, the collected urine sample is the first urine void after administration of the marker. The urine sample is then analyzed for any analyte of interest (e.g., illicit and performance enhancing drugs) and the presence and/or amount of the marker substances is determined. Authentic urine samples will have contain the specific marker substances and, optionally, in the correct ratios. An inauthentic sample either will lack any marker substances (i.e., substitution with "clean" urine) or will lack the correct marker substances that are identifiable to the subject (i.e., substitution with urine from a different subject who consumed a different marker).

Key to this methodology is that the specific identity of the marker substances is unknown to the subject and, preferably, unknown to the sample collectors. This is most conveniently done by providing one or more markers (i.e., set of markers) which are labeled solely with a unique identifier for correlating the subject with the urine sample. The identifier should contain no other information as to the marker substance content, thereby resulting in a double blind collection process in which neither the subject nor the administrator/sample collector knows the specific contents of the marker.

This methodology provides several advantages. First, as noted above, the sample collection process may be double blinded, or even triple blinded in which the testing laboratory does not know the subjects' identity or the expected marker profile. The unblinding process may then be done in a controlled manner and by a limited number of people under appropriate supervision. Second, this method eliminates the need for the subject to be supervised during the urine collection process. It is only necessary that the subject is observed to consume the marker which is much less labor intensive and time-consuming than supervising the actual urine collection process. Additionally, following marker administration, the subject is then free to collect the urine sample (preferably the first urine void) with privacy and at a time of their convenience, within the bounds of complete excretion and elimination of the marker substances. In practice, subjects likely will be required to stay within a controlled area during the sample collection process and will be allowed to leave upon tendering their urine sample. Third, the presence of a marker internal to the urine sample reduces or eliminates the problem of samples which are mislabeled or misordered by the analytical facility which, in the absence of an internal marker, may result in a specific sample being identified to the wrong individual. In other words, any particular urine sample can be identified to an individual by determining the marker and looking up the administration record.

Marker Production and Selection of Marker Substances

Ideal marker substances for use in the compositions and methods of the invention should fulfill several or all of the following criteria:

(1) not harmful to the subjects,
(2) preferably listed as an inactive ingredient by the FDA or other relevant regulatory agency,
(3) has no pharmacological effect in concentrations used,
(4) not metabolized or metabolized to a unique metabolite,
(5) chemically stable and suitable for long-term storage (e.g., at least 6 months) in the marker formulation,
(6) rapidly absorbed from gastrointestinal tract,
(7) rapidly excreted into the urine by the kidneys,
(8) may be used at convenient dosage sizes (i.e., functions as a marker when administered in a convenient volume or formulation),
(9) not easily accessible or widely available to laypeople,
(10) easily detectable in urine using standard analytical techniques,
(11) lacks drug interactions,
(12) not normally present in the urine of the subjects (i.e., not an endogenous molecule or a normal dietary component), and
(13) present in different chemical forms having similar chemical and biological properties.

In some embodiments, marker sets are constructed from a plurality of individual marker substances (e.g., 2, 3, 4, 5, 6, 7, 8, 9, 10, or more marker substances). The advantage of using multiple marker substances to construct a marker set is that a very large number of unique markers can be constructed from a relative small number of marker substances. Specifically, $2^n-1$ different markers may be constructed, where n is the number of unique marker substances available. For example, 63 markers can be made from only six marker substances and 1023 markers can be made from only ten marker substances. When testing groups of individuals, it is desirable that every individual in the group is administered a unique marker to eliminate the problem of mixing up samples (intentionally or inadvertently) from individuals administered the same marker.

Useful marker substances include, for example,
polyethylene glycol (PEG)
acesulfame and salts thereof (e.g, acesulfame potassium)
acetylated monoglycerides
butylparaben (butyl parahydroxybenzoate)
povidone (polyvinylpyrrolidone)
copovidone (crospovidone)
gelucires (mixture of glycerides and esters of polyethylene glycol including, for example, mono-, di- and triglycerides and mono- and diesters of PEG; e.g., gelucire 33/01, 37/02, 39/01, 43/01, 44/14, 50/02, 50/13, 53/10, and 62/02)
hypromelloses (hydroxypropyl methyl cellulose)
polycarbophil (polyacrylic acid cross-linked with divinyl glycol)
polydextrose, and
tartaric acid and salts thereof (2,3-dihydroxybutanedioic acid)

Particularly useful as markers from among potential marker substances are those that are polymers such as PEG, povidone, copovidone, the gelucires, and polycarbophil. Multiple marker substances can be synthesize based on a single polymer type merely by varying the polymer length (molecular weight). The number of different marker substances derived from a single polymer is limited only by the mass resolution of the analytic methodology and the absorption/excretion properties of the polymers (e.g., if sufficiently large, certain polymers may not be absorbed from the gastrointestinal tract). One advantage of using a single polymer type, having different molecular weights, as a marker substances is that each species is expected to have approximately the same absorption, distribution, and excretion profiles, as well as being detectable using the same analytical techniques.

It is also possible to increase the number of marker substances without increasing the number of distinct chemical species by labeling any given marker substance with one or more stable isotopes. Isotope labeling may vary in the number or type of isotopic label used. This technique is necessarily paired with a detection methodology that is capable of detecting and distinguishing identical chemical structures based on differences in molecular weight (e.g., mass spectrometry).

The number of unique markers may be further increased for any given number of marker substances by varying the relative or absolute amounts of the marker substances relative to each other. This is most preferably done for marker substances having stable isotopes incorporated into the same chemical structure or for polymers varying only in molecular weight (i.e., number of repeating monomeric units). For example, in its simplest form, when only a single marker substance is used which is either unlabeled or labeled with a single stable isotope, represented generically as X and X', a marker set may be constructed by varying the ratios of X to X' as follows:

| Marker # | Relative Amount of Marker Substance | |
| --- | --- | --- |
|  | X | X' |
| 1 | 1 | 0 |
| 2 | 0 | 1 |
| 3 | 1 | 1 |
| 4 | 1 | 2 |
| 5 | 1 | 3 |
| 6 | 1 | 4 |
| 7 | 2 | 1 |
| 8 | 3 | 1 |
| 9 | 4 | 1 |

Alternatively, for example, X and X' may represent polymers of different molecular weights (e.g., monodispersed PEG 400 and PEG 800) or two chemically distinct marker substances (e.g., a PEG and a butylparaben). The ratios of the paired marker substances are not limited to those ratios shown in the table above but may include any convenient ratio or combination of ratios such as 5:1, 10:1, 15:1, 20:1, or more. The only practical limits are those of convenience and detectability. Furthermore, the strategy of constructing unique markers based on the relative ratios of marker substances is not limited to pairs of marker substances but instead can be extended to varying the relative ratios of 3, 4, 5, 6, 7, 8, or more marker substances, thereby significantly increasing the total number of unique markers available within a set, without increasing the number of chemically distinct marker substances.

When using polymers as marker substances (e.g., PEG, including glucires, celluloses, polyacrylic acids, polydextrose, etc.), the molecular weight of the polymers is preferably less than about 5000 Da, 4000 Da, 3000 Da, 2000 Da, 1,500 Da, 1000 Da, 900 Da, 800 Da, 700 Da, 600 Da, 500 Da, or 400 Da, and/or greater than about 100 Da, 150 Da, 200 Da, 250 Da, 300 Da, 400 Da, and 500 Da. Typically, the polymer has at least about 2, 3, 4, 5, 7, 10, 15, 20, 25, 30, 40, 50, 75, or 100 repeating monomeric units and/or not more than about 15, 25, 50, 75, 100, 150, 200, 250, or 500 repeating monomeric units.

Quantification of Marker Substances in Urine Samples

Any marker substance utilized in the methods and compositions of this invention may be detected in urine samples using any convenient detection/quantification methodology. It is generally preferred to use methodologies that are automated and can simultaneously applicable to several or all marker substances. Mass spectrometry (MS), generally, and LC-MS/MS, specifically, are useful detection methodologies because these techniques have very high sensitivity and specificity, can be quantitative, can detect small changes in molecular weight (e.g., when using multiple polymers differing only in the number of repeating monomeric units and/or stable isotopic labels), and may be applicable to further detect urinary analytes of interest. Specific analytical techniques useful for detecting and/or quantifying the marker substances of the invention include, but are not limited to, those referenced in the following table.

| | |
|---|---|
| Acesulfame | Ordonez et al., J. Chromatogr. A., 1256: 197-205, 2012 |
| | Berset et al., Chemosphere 88: 563-569, 2012 |
| Acetylated monoglycerides | Falardeau et al., Anal. Biochem. 208: 311-316, 1993 |
| | Nebel et al., Anal Chem. 80: 8712-8716, 2008 |
| Butylparaben | Jondeau-Cabaton et al., Environ. Sci. Pollut. Res. Int. 20: 2705-2720, 2013 |
| | Casas Ferreira et al., Anal. Bioanal. Chem. 399: 945-953, 2011 |
| Povidone | Raith et al., Pharm Res. 19: 556-560, 2002 |
| Copovidone | Trimpin et al., J. Chromatogr. A. 938: 67-77, 2001 |
| Gelucire | Perez Hurtado et al., Anal. Chem. 84: 8579-8586, 2012 |
| Hypromelloses | Cuers et al., Anal Bioanal. Chem., Jun. 18, 2013 |
| | Schargerlof et al., Biomacromolecules 7: 3474-3481, 2006 |
| | Momcilovic et al., Biomacromolecules 6: 2793-2799, 2005 |
| Polycarbophil | McCormack et al., J. Occup. Environ. Hyg. 8: 215-225, 2011 |
| Polydextrose | Lahtinen et al., Biosci. Biotechnol. Biochem. 74: 2016-2021, 2010 |
| Tartaric acid | Tonner et al., J. Phys. Chem. A. 116: 4789-4800, 2012 |

Preventing Marker Diversion

The advantage of the present method in allowing unsupervised urine collection by subjects has the potential to induce other forms of cheating which may include "marker diversion." It is possible that the subject either will not consume the administered marker and/or will sequester some of the marker formulation without ingestion. This sequestration may come in the form of pill splitting or capturing a liquid marker formulation in a separate vessel prior to ingestion or even by hiding a sponge or other absorbant material in the mouth. The subject may then attempt to add the retained marker formulation to a "clean" urine sample during the unsupervised collection process. This form of cheating by urine substitution and marker replacement may be detected by further incorporating a metabolizable or non-absorbable marker substance (i.e., a secondary marker substance) into the marker formulation. The secondary marker substance therefore will not normally be present in a urine sample. Thus, if the secondary marker is detected in the urine sample, urine substitution is proven. The secondary marker is not used for identification purposes (i.e., for uniquely identifying a urine sample to an individual) and therefore may be the same for all markers in the set. Alternatively, several secondary markers may be used within a set. Suitable markers include ordinarily metabolizable carbohydrates, such as sucrose and lactose. Alternatively, non-absorbable markers include soluble dyes or polymers such as beta-glucans.

Marker Formulations

For use in human and animal subjects, the markers may be formulated as is typical of pharmaceutical or veterinary compositions, preferably for oral administration. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

The makers may be present in amounts totaling 1-95% by weight of the total weight of the composition and the composition may further contain a pharmaceutically acceptable matrix of excipients (e.g., fillers, diluents, lubricants, and/or glidants) provided in a dosage form that is suitable for oral administration. Thus, the marker composition may be in the form of, e.g., hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, suspensions, syrups, or sprinkles. The compositions may be formulated according to conventional pharmaceutical practice.

Other Embodiments

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Terms and phrases used in this document, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; and adjectives such as 'known,' 'normal,' 'standard,' and terms of similar meaning should not be construed as limiting the item described to a given time period or to an item available as of a given time, but instead should be read to encompass known, normal, or standard technologies that may be available or known now or at any time in the future. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more,' 'at least,' 'but not limited to,' or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for marking a group of urine samples to identify for each sample the individual who provided that sample, comprising:
   (a) orally administering a marker to each individual in a group of individuals, wherein each individual in the group is administered a unique marker, wherein at least one marker comprises one or more marker substances that differ in chemical nature, molecular weight, relative amount, or a combination thereof; and wherein at least one of the markers comprises a marker substance selected from the group consisting of acesulfame, an acetylated monoglyceride, butylparaben, povidone, copovidone, crospovidone, gelucire, hypromelloses, polycarbophil, polydextrose, tartaric acid or a salt thereof, and derivatives thereof;
   (b) waiting for a length of time sufficient for the marker substances to be present in the urine of the individuals;
   (c) collecting a urine sample from each individual;
   (d) detecting the presence or amount of the marker substances in the urine samples; and
   (e) using the presence or amount of the marker substances identified in each sample to identify the individual who provided the sample.

2. The method of claim 1, wherein at least one of the markers further comprises at least one polyethylene glycol.

3. The method of claim 2, wherein the at least one polyethylene glycol is a monodispersed polyethylene glycol.

4. The method of claim 2, wherein the at least one polyethylene glycol is a polydispersed polyethylene glycol.

5. The method of claim 1, wherein at least one marker comprises at least two marker substances selected from the group consisting of acesulfame, an acetylated monoglyceride, butylparaben, copovidone, crospovidone, gelucire, hypromelloses, polycarbophil, polydextrose, povidone, and tartaric acid or a salt thereof.

6. The method of claim 1, wherein at least one of said marker substances in at least one of the markers is excreted unmetabolized in the urine of the individual.

7. The method of claim 1, wherein said method further comprises detecting the presence or amount of an analyte in the urine sample from at least one individual within the group of individuals.

8. The method of claim 7, wherein the analyte is selected from the group consisting of a pharmaceutical, a drug of abuse, nicotine, and a performance enhancing drug.

9. The method of claim 8, wherein the drug of abuse is cocaine or heroin.

10. A method for marking a urine sample to identify the individual who provided that sample, comprising:
    (a) orally administering a marker to an individual, wherein the marker comprises one or more marker substances selected from the group consisting of acesulfame, an acetylated monoglyceride, butylparaben, povidone, copovidone, crospovidone, gelucire, hypromelloses, polycarbophil, polydextrose, tartaric acid or a salt thereof, and derivatives thereof;
    (b) waiting for a length of time sufficient for the one or more marker substances to be present in the urine of the individual;
    (c) collecting a urine sample from each individual;
    (d) detecting the presence or amount of the one or more marker substances in the urine samples; and
    (e) using the presence or amount of the marker substances identified that the urine sample was obtained from the individual to whom the marker was administered.

11. The method of claim 10, wherein the marker further comprises at least one polyethylene glycol.

12. The method of claim 11, wherein the at least one polyethylene glycol is a monodispersed polyethylene glycol.

13. The method of claim 10, wherein the marker comprises at least two marker substances selected from the group consisting of acesulfame, an acetylated monoglyceride, butylparaben, copovidone, crospovidone, gelucire, hypromelloses, polycarbophil, polydextrose, povidone, and tartaric acid or a salt thereof.

14. The method of claim 10, and wherein at least one of the marker substances is excreted unmetabolized in the urine of the individual.

* * * * *